United States Patent [19]

Bartmann et al.

[11] Patent Number: 5,643,495
[45] Date of Patent: Jul. 1, 1997

[54] 1,2,2,2-TETRAFLUOROETHYL ETHERS, AND LIQUID-CRYSTALLINE MEDIUM

[75] Inventors: Ekkehard Bartmann, Erzhausen; Ulrich Finkenzeller, Plankstadt, both of Germany

[73] Assignee: Merck Patent Gesellschaft mit Beschrankter Haftung, Darmstadt, Germany

[21] Appl. No.: 525,527

[22] PCT Filed: Mar. 11, 1994

[86] PCT No.: PCT/EP94/00767

§ 371 Date: Sep. 12, 1995

§ 102(e) Date: Sep. 12, 1995

[87] PCT Pub. No.: WO94/21747

PCT Pub. Date: Sep. 29, 1994

[30] Foreign Application Priority Data

Mar. 13, 1993 [DE] Germany .................. 43 08 028.6

[51] Int. Cl.$^6$ .................. C09K 19/30; C09K 19/12; C07C 25/13; C07C 43/02

[52] U.S. Cl. .................. 252/299.63; 252/299.61; 252/299.62; 252/299.66; 252/299.67; 349/182; 544/298; 549/369; 549/370; 560/65; 560/100; 560/102; 570/127; 570/129; 570/144; 568/588; 568/634

[58] Field of Search .................. 252/299.01, 299.61, 252/299.62, 299.63, 299.64, 299.65, 299.66, 299.67; 359/103; 570/127, 129, 144; 544/298; 549/369, 370; 560/65, 100, 102; 568/588, 584, 634

[56] References Cited

U.S. PATENT DOCUMENTS

| 5,051,527 | 9/1991 | Suzuki et al. | 252/299.01 |
| 5,389,289 | 2/1995 | Rieger et al. | 252/299.01 |
| 5,409,637 | 4/1995 | Rieger et al. | 252/299.63 |
| 5,422,035 | 6/1995 | Bartmann et al. | 252/299.01 |
| 5,458,806 | 10/1995 | Bartmann et al. | 252/299.63 |

FOREIGN PATENT DOCUMENTS

4101600  8/1991  Germany .

*Primary Examiner*—Shean C. Wu
*Attorney, Agent, or Firm*—Millen, White, Zelano, & Branigan, P.C.

[57] ABSTRACT

1,2,2,2-Tetrafluoroethyl ethers of the formula I $$R-(A^1-Z^1)_m-A^2-Z^2A^3-O-CHF-CF_3 \quad (I)$$

are suitable as components of liquid-crystalline media wherein

R is H, a substituted or unsubstituted alkyl or alkenyl radical having 1 to 15 carbon atoms, $A^1$ and $A^2$ are each, independently of one another, a (a) trans-1,4-cyclohexylene radicals and derivatives thereof in which, in addition, one or more non-adjacent $CH_2$ groups is optionally replaced by —O— and/or —S—, (b) 1,4-phenylene radicals and derivatives thereof in which, in addition, one or two CH groups is optionally replaced by N, or (c) radical from the group consisting of 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, wherein radicals (a) and (b) are optionally substituted by one or two fluorine atoms, $Z^1$ and $Z^2$ are each, independently of one another, —CO—O—, —O—CO—, —CH$_2$O—, —OCH$_2$—, —CH$_2$CH$_2$—, —CH=CH—, —C≡C— or a single bond, and one of the radicals $Z^1$ and $Z^2$ is optionally —(CH$_2$)$_4$— —CH=CH—CH$_2$CH$_2$—, X is H, F or Cl and is 0, 1 or 2.

15 Claims, No Drawings

1,2,2,2-TETRAFLUOROETHYL ETHERS, AND LIQUID-CRYSTALLINE MEDIUM

This application is a 371 of PCT/EP94/00767 filed Mar. 11, 1994.

The invention relates to 1,2,2,2-tetrafluoroethyl ethers of the formula I $$R-(A^1-Z^1)_m-A^2-Z^2-A^3-O-CHF-CF_3 \quad I$$

in which

R is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—,

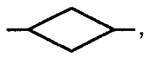

—CO—, —CO—O—, —O—CO— or —O—CO—O— in such a way that O atoms are not linked directly to one another, $A^1$, $A^2$ and $A^3$ are each, independently of one another, (a) a trans-1,4-cyclohexylene radical in which, in addition, one or more non-adjacent $CH_2$ groups can be replaced by —O— and/or —S—, (b) a 1,4-phenylene radical in which, in addition, one or two CH groups can be replaced by N, (c) a radical from the group consisting of 1,4-cyclohexenylene, 1,4-bicyclo[2.2.2]octylene, piperidine-1,4-diyl, naphthalene-2,6-diyl, decahydronaphthalene-2,6-diyl and 1,2,3,4-tetrahydronaphtalene-2,6-diyl, where the radicals (a) and (b) can be substituted by one or two fluorine atoms, $Z^1$ and $Z^2$ are each, independently of one another, —CO—O—, —O—CO—, —$CH_2$O—, —O$CH_2$—, —$CH_2CH_2$—, —CH=CH—, —C≡C— or a single bond, and one of the radicals $Z^1$ and $Z^2$ is alternatively —$(CH_2)_4$— or —CH=CH—$CH_2CH_2$—, and m is 0, 1 or 2.

The invention furthermore relates to the use of these compounds as components of liquid-crystalline media and to liquid-crystal and electro-optical display elements containing the liquid-crystalline media according ing to the invention.

The compounds of the formula I can be used as components of liquid-crystalline media, in particular for displays based on the principle of the twisted cell, the guest-host effect, the effect of deformation of aligned phases or the effect of dynamic scattering.

The invention had the object of finding novel, stable, liquid-crystalline or mesogenic compounds which are suitable as components of liquid-crystalline media and in particular have at the same time comparatively low viscosity and relatively high dielectric anisotropy.

It has now been found that compounds of the formula I are eminently suitable as components of liquid-crystalline media. In particular, they have comparatively low viscosities. They can be used to obtain stable liquid-crystalline media having a broad mesophase range and advantageous values for the optical and dielectric anisotropy. Furthermore, these media have very good low-temperature behaviour.

In the general formula, WO 88/00335 covers the compounds of the formula I, but the compounds according to the invention are not mentioned therein.

DE-A 41 04 126 describes compounds containing a terminal O—$CH_2$—$CF_3$ or O—$CH_2$—$CH_2F$ group, such as, for example,

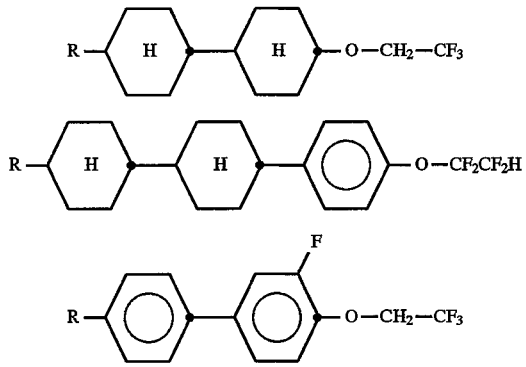

However, in view of the very wide range of areas of application of such compounds having high Δε, it was desirable to have available further compounds of high nematogeneity which have properties precisely customized to the particular applications.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials from which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favourably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystal display elements, in particular electro-optical display elements, containing media of this type.

For reasons of simplicity, $A^3$ below is a radical of the formula

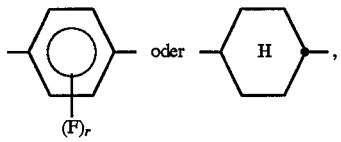

where r is 0, 1 or 2, Y is O—CH—$CF_3$, Cyc denotes a 1,4-cyclohexyl radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo-[2.2.2.]octylene radical, where Cyc and/or Phe can be unsubstituted or monosubstituted or disubstituted by F or CN.

$A^1$, $A^2$ and $A^3$ are preferably selected from the group consisting of Cyc, Che, Phe, PYr, Pyd and Dio, it being preferred that only one of the radicals $A^1$, $A^2$ and $A^3$ present in the molecule is Che, Phe, Pyr, Pyd or Dio.

Accordingly, the compounds of the formula I cover bicyclic compounds of the subformulae Ia and Ib:

| | |
|---|---|
| R—$A^2$—$A^3$—Y | Ia |
| R—$A^2$—$Z^2$—$A^3$—Y | Ib | tricyclic compounds of the subformulae Ic to If:

| | |
|---|---|
| R—$A^1$—$A^2$—$A^3$—Y | Ic |
| R—$A^1$—$Z^1$—$A^2$—$Z^2$—$A^3$—Y | Id |
| R—$A^1$—$Z^1$—$A^2$—$A^3$—Y | Ie |
| R—$A^1$—$A^2$—$Z^2$—$A^3$—Y | If | and tetracyclic compounds of the subformulae Ig to Im:

| | |
|---|---|
| R—$A^1$—$A^1$—$A^2$—$A^3$—Y | Ig |
| R—$A^1$—$Z^1$—$A^1$—$A^2$—$A^3$—Y | Ih |
| R—$A^1$—$A^1$—$Z^1$—$A^2$—$A^3$—Y | Ii |
| R—$A^1$—$A^1$—$A^2$—$Z^2$—$A^3$—Y | Ij |
| R—$A^1$—$Z^1$—$A^1$—$Z^1$—$A^2$—$A^3$—Y | Ik |
| R—$A^1$—$A^1$—$Z^1$—$A^2$—$Z^2$—$A^3$—Y | Il |
| R—$A^1$—$Z^1$—$A^1$—$Z^1$—$A^2$—$Z^2$—$A^3$—Y | Im |

Of these, particular preference is given to the compounds of the subformulae Ia, Ib, Ic, Id, Ie, If, Ii and Il.

Preferred compounds of the subformula Ia are those of the subformulae Iaa to Iaf:

| | |
|---|---|
| R—Phe—$A^3$—Y | Iaa |
| R—Dio—$A^3$—Y | Iab |
| R—Pyr—$A^3$—Y | Iac |
| R—Pyd—$A^3$—Y | Iad |
| R—Cyc—$A^3$—Y | Iae |
| R—Che—$A^3$—Y | Iaf |

Of these, those of the formulae Iaa and Iae are particularly preferred.

Preferred compounds of the subformula Ib are those of the subformulae Iba to Ibc:

| | |
|---|---|
| R—Cyc—$CH_2CH_2$—$A^3$—Y | Iba |
| R—Cyc—COO—$A^3$—Y | Ibb |
| R—Phe—COO—$A^3$—Y | Ibc |

Preferred compounds of the subformula Ic are those of the subformulae Ica to Icn:

| | |
|---|---|
| R—Phe—Phe—$A^3$—Y | Ica |
| R—Phe—Pyd—$A^3$—Y | Icb |
| R—Phe—Dio—$A^3$—Y | Icc |
| R—Cyc—Cyc—$A^3$—Y | Icd |
| R—Phe—Cyc—$A^3$—Y | Ice |
| R—Cyc—Pyd—$A^3$—Y | Icf |
| R—Pyd—Phe—$A^3$—Y | Icg |
| R—Pyr—Phe—$A^3$—Y | Ich |
| R—Phe—Pyr—$A^3$—Y | Ici |
| R—Cyc—Pyr—$A^3$—Y | Icj |
| R—Cyc—Phe—$A^3$—Y | Ick |
| R—Dio—Phe—$A^3$—Y | Icl |
| R—Che—Phe—$A^3$—Y | Icm |
| R—Phe—Che—$A^3$—Y | Icn |

Of these, those of the formulae Ica, Icd, Ice and Ick are particularly preferred.

Preferred compounds of the subformula Ib are those of the subformulae Ida to Idk:

| | |
|---|---|
| R—Phe—$Z^1$—Phe—$Z^2$—$A^3$—Y | Ida |
| R—Phe—$Z^1$—Dio—$Z^2$—$A^3$—Y | Idb |
| R—Cyc—$Z^1$—Cyc—$Z^2$—$A^3$—Y | Idc |
| R—Cyc—$Z^1$—Pyr—$Z^2$—$A^3$—Y | Idd |
| R—Pyd—$Z^1$—Phe—$Z^2$—$A^3$—Y | Ide |
| R—Phe—$Z^1$—Pyd—$Z^2$—$A^3$—Y | Idf |
| R—Pyr—$Z^1$—Phe—$Z^2$—$A^3$—Y | Idg |
| R—Phe—$Z^1$—Pyr—$Z^2$—$A^3$—Y | Idh |
| R—Phe—$Z^1$—Cyc—$Z^2$—$A^3$—Y | Idi |
| R—Cyc—$Z^1$—Phe—$Z^2$—$A^3$—Y | Idj |
| R—Dio—$Z^1$—Phe—$Z^2$—$A^3$—Y | Idk |

Preferred compounds of the subformula Ie are those of the subformulae Iea to Iej:

| | |
|---|---|
| R—Pyr—$Z^1$—Phe—$A^3$—Y | Iea |
| R—Dio—$Z^1$—Phe—$A^3$—Y | Ieb |
| R—Phe—$Z^1$—Phe—$A^3$—Y | Iec |
| R—Cyc—$Z^1$—Phe—$A^3$—Y | Ied |
| R—Phe—$Z^1$—Cyc—$A^3$—Y | Iee |
| R—Cyc—$Z^1$—Cyc—$A^3$—Y | Ief |
| R—Phe—$Z^1$—Dio—$A^3$—Y | Ieg |
| R—Pyd—$Z^1$—Phe—$A^3$—Y | Ieh |
| R—Phe—$Z^1$—Pyr—$A^3$—Y | Iei |
| R—Cyc—$Z^1$—Pyr—$A^3$—Y | Iej |

Preferred compounds of the sub formula If are those of the subformulae Ifa to Ifn:

| | |
|---|---|
| R—Pyr—Phe—$Z^2$—$A^3$—Y | Ifa |
| R—Pyr—Phe—$OCH_2$—$A^3$—Y | Ifb |
| R—Phe—Phe—$Z^2$—$A^3$—Y | Ifc |
| R—Phe—Phe—OOC—$A^3$—Y | Ifd |
| R—Cyc—Cyc—$Z^2$—$A^3$—Y | Ife |
| R—Cyc—Cyc—$CH_2CH_2$—$A^3$—Y | Iff |
| R—Pyd—Phe—$Z^2$—$A^3$—Y | Ifg |
| R—Dio—Phe—$Z^2$—$A^3$—Y | Ifh |
| R—Phe—Cyc—$Z^2$—$A^3$—Y | Ifi |
| R—Phe—Pyd—$Z^2$—$A^3$—Y | Ifj |
| R—Che—Phe—$Z^2$—$A^3$—Y | Ifk |
| R—Phe—Che—$Z^2$—$A^3$—Y | Ifl |
| R—Cyc—Phe—$Z^2$—$A^3$—Y | Ifm |
| R—Cyc—Phe—OOC—$A^3$—Y | Ifn |

Preference is also given to compounds of the formula I and of all subformulae in which $A^1$, $A^2$ and/or $A^3$ is 1,4-phenylene which is monosubstituted or disubstituted ed by F or monosubstituted by CN. These are, in particular, 2-fluoro-1,4-phenylene, 3-fluoro-1,4-phenylene and 3,5-difluoro-1,4-phenylene and also 2-cyano-1,4-phenylene and 3-cyano-1,4-phenylene.

$A^3$ is preferably 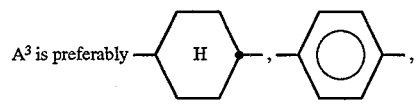

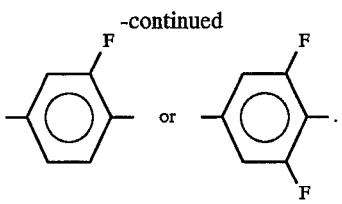

$Z^1$ and $Z^2$ are preferably a single bond, —CO—O—, —O—CO— or —CH$_2$CH$_2$—, secondarily preferably —CH$_2$O— or —OCH$_2$—.

If one of the radicals $Z^1$ and $Z^2$ is —(CH$_2$)$_4$— or —CH=CH—CH$_2$CH$_2$—, the other radical $Z^1$ or $Z^2$ (if present) is preferably a single bond.

Preferred compounds of this type conform to the subformula I'

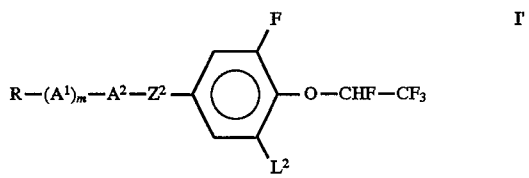

in which $Z^2$ is —(CH$_2$)$_4$— or —CH=CH—CH$_2$CH$_2$—, and R, A$^1$, A$^2$ and m are as defined under the formula I, and L$^2$ is H or F. The preferred meanings of R, A$^1$, A$^2$ and m also correspond to those for the compounds of the formula I.

m is preferably 1 or 0, particularly preferably 0.

If R is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoky, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxaheyxl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8 - or 9-oxadecyl.

If R is an alkyl radical in which one CH$_2$ group has been replaced by —CH=CH—, this may be straight-chain or branched. It is preferably straight-chain and has 2 to 10 carbon atoms. Accordingly it is in particular vinyl, prop-1- or -2-enyl, but-1-, -2- or -3-enyl, pent-1-2-, -3- or -4-enyl, hex-1-, -2-, -3-, -4- or -5-enyl, hept-1-, -2-, -3-, -4-, -5- or -6-enyl, oct-1-, -2-, -3-, -4-, 5-, -6- or -7-enyl, non-1-, -2-, -3-, -4-, -5-, -6-, -7-or -8-enyl, or dec-1-, -2-, -3-, -4-, -5-, -6-, -7-, -8- or -9-enyl.

If R is an alkyl radical in which one CH$_2$ group has been replaced by —O— and one has been replaced by —CO—, these are preferably adjacent. This thus contains one acyloxy group —CO—O— or one oxycarbonyl group —O—CO—. This is preferably straight-chain and has 2 to 6 carbon atoms.

Accordingly it is in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxy-propyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl) ethyl, 2-(propoxycarbonyl)ethyl, 3-(methoxycarbonyl)propyl, 3-(ethoxycarbonyl ) propyl or 4-(methoxycarbonyl)butyl.

If R is an alkyl radical in which one CH$_2$ group has been replaced by unsubstituted or substituted —CH=CH— and an adjacent CH$_2$ group has been replaced by CO or CO—O or O—CO—, this may be straight-chain or branched. It is preferably straight-chain and has 4 to 13 carbon atoms. Accordingly it is in particular acryloyloxmethyl, 2-acryloyloxyethyl, 3-acryloyl-oxypropyl, 4-acryloyloxybutyl, 5-acryloyloxypentyl, 6-acryloyloxyhexyl, 7-acryloyloxygeptyl, 8-acryloyl-oxyoctyl, 9-acryloyloxynonyl, 10-acryloyloxydecyl, methacryl oyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or CF$_3$, this radical is preferably straight-chain and the substitution by CN or CF$_3$ is in the ω-position.

If R is an alkyl or alkenyl radical which is at least monosubstituted by halogen, this radical is preferably ably straight-chain and halogen is preferably. F or Cl. In the case of multiple substitution, halogen is preferably F. The resulting radicals also include perfluorinated radicals. In the case of monosubstitution, the fluorine or chlorine substituent can be in any desired position, but is preferably in the ω-position.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having S$_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutoxy), 2-methylpentyl, 3-methylpentyl, 2-ethylhexyl, 2-propylpentyl, isopropoxy, 2-methyl -propoxy, 2-methylbutoxy, 3-methylbutoxy, 2-methylpentoxy, 3-methylpentoxy, 2-ethylhexoxy, 1 -methylhexoxy and 1-methylheptoxy.

If R is an alkyl radical in which two or more CH$_2$ groups have been replaced by —O— and/or —CO—O—, this may be straight-chain or branched. It is preferably branched and has 3 to 12 carbon atoms. Accordingly it is in particular biscarboxymethyl, 2,2-biscarboxyethyl, 3,3-biscarboxypropyl, 4,4-bis-carboxybutyl, 5,5-biscarboxypentyl, 6,6-bis-carboxyhexyl, 7,7-biscarboxyheptyl, 8,8-biscarboxy-octyl, 9,9-biscarboxynonyl, 10,10-biscarboxydecyl, bis (methoxycarbonyl)methyl, 2,2-bis(methoxycarbonyl)ethyl, 3,3-bis(methoxycarbonyl)propyl, 4,4-bis(-methoxycarbonyl)butyl, 5,5-bis(methoxy-carbonyl)pentyl, 6,6-bis(methoxycarbonyl)hexyl, 7,7-bis(methoxycarbonyl) heptyl, eptyl, 8,8-bis(methoxycarbonyl)-octyl, bis (ethoxycarbony-1) methyl, 2,2-bis(ethoxy-carbonyl)ethyl, 3,3-bis(ethoxycarbonyl)propyl, 4,4-bis(ethoxycarbonyl) butyl or 5,5-bis(ethoxycarbonyl)hexyl.

Compounds of the formula I which contain wing groups R which are suitable for polycondensations are suitable for the preparation of liquid-crystalline polycondensates.

The formula I covers the racemates of these compounds and the optical antipodes, and mixtures thereof.

Of these compounds of the formula I and of the subformulae, preference is given to those in which at least one of the radicals present therein has one of the preferred meanings mentioned.

In the compounds of the formula I, preference is given to the stereoisomers in which the rings Cyc and Piperidine are trans-1,4-disubstituted. Those of the abovementioned formulae which contain one or more groups Pyd, Pyr and/or Dio in each case include the two 2,5-positional isomers.

Preferred smaller groups of compounds are those of the subformulae I1 to I19:

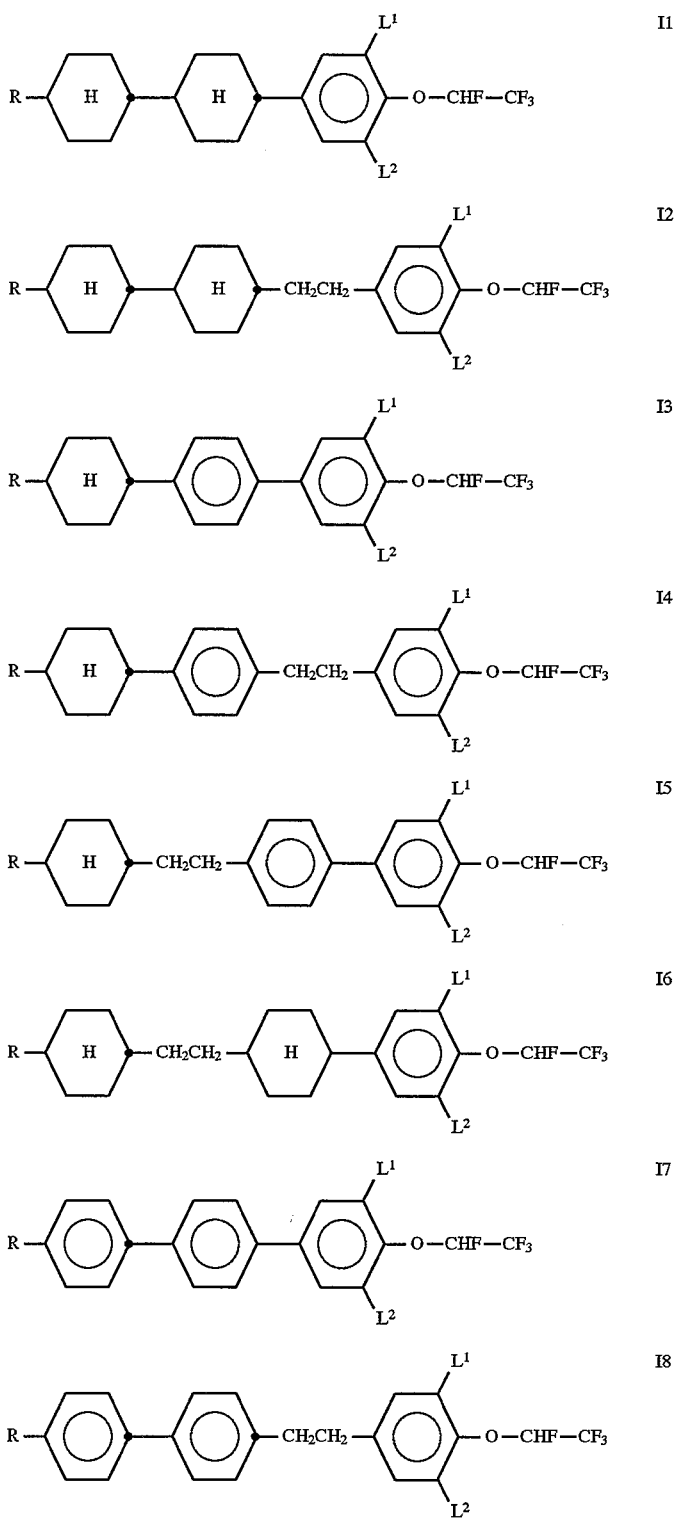

-continued
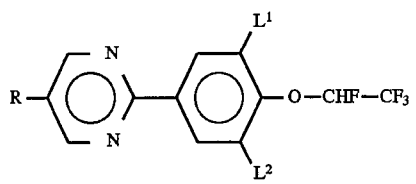
I9
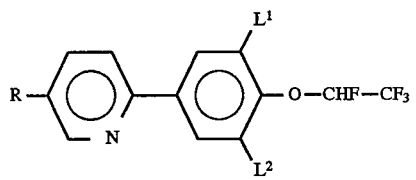
I10
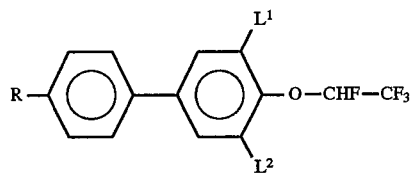
I11
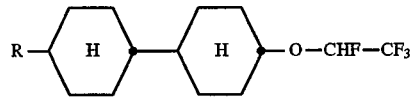
I12
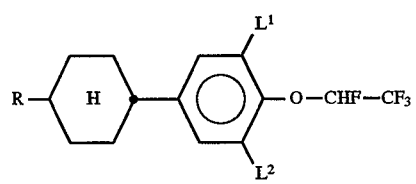
I13
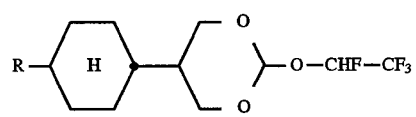
I14
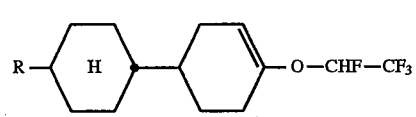
I15
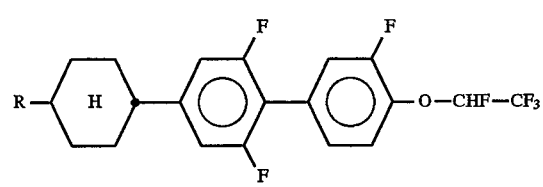
I16
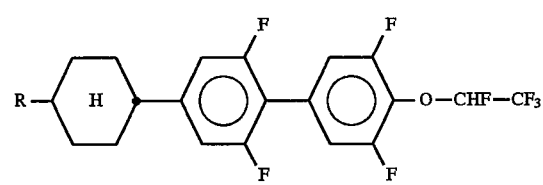
I17
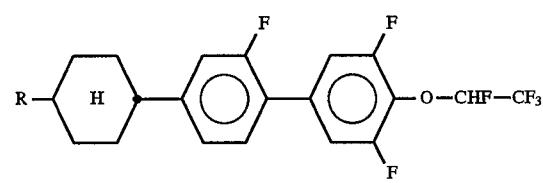
I18

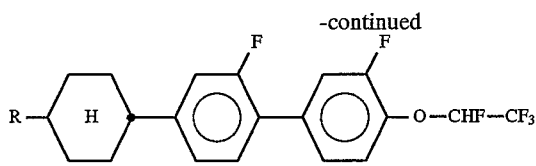

The 1,4-cyclohexenylene group preferably has the following structures:

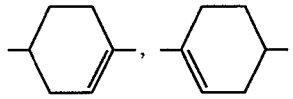

The compounds of the formula I are prepared by methods known per se, as described in the literature (for example in the standard works such as Houben-Weyl, Methoden der Organischen Chemie, Georg-Thieme-Verlag, Stuttgart), to be precise under reaction conditions which are known and suitable for said reactions.

Use may also be made of variants which are known per se, but are not mentioned here in greater detail.

The novel compounds can be prepared, for example, by metalating a compound of the formula II

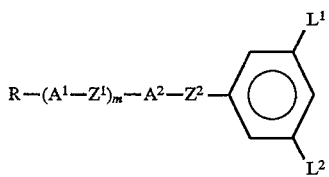

in which R, $A^1$, $A^2$, $Z^1$, $Z^2$ and m are as defined above, and $L^1$ and $L^2$ are H or F, as shown in the reaction scheme below, and subsequently reacting the product with 1,2,2,2-tetrafluoro-1-iodoethane:

Scheme 1

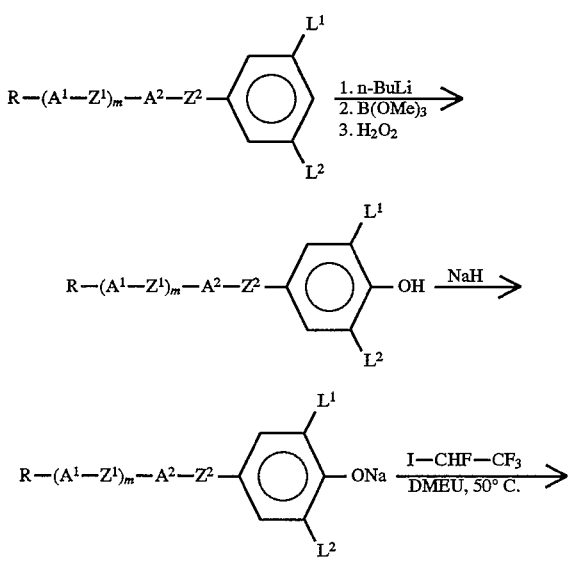

Scheme 1

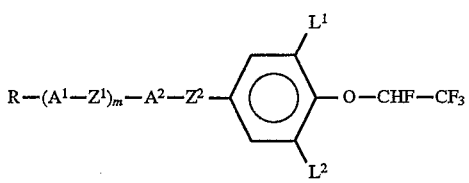

Scheme 2

($L^{1-4}$ = H or F; R* = halogen or formyl)

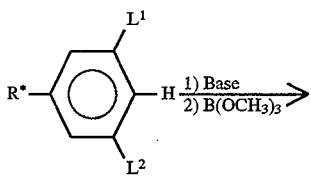

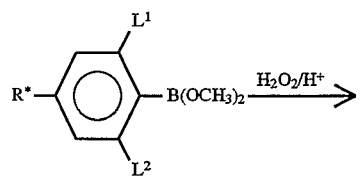

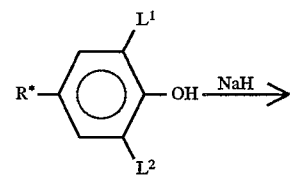

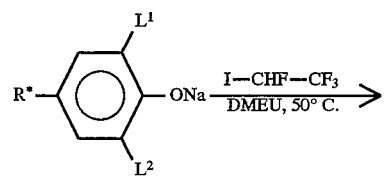

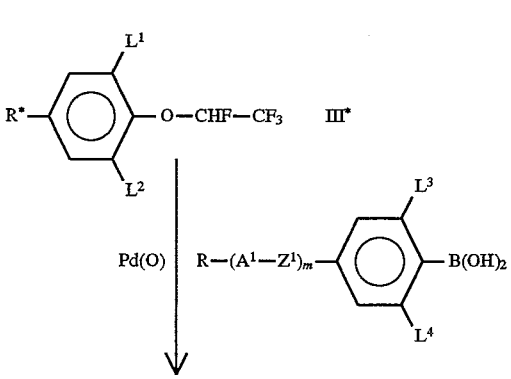

-continued
Scheme 2

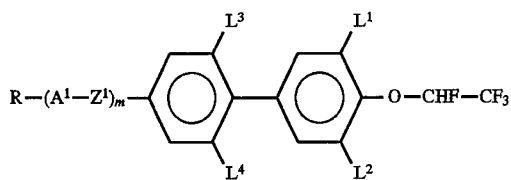

The invention also relates to a process for the preparation of substituted 1,2,2,2-tetrafluoroethoxybenzene from the corresponding phenoxide, which is characterized in that the phenoxide is reacted with 1,2,2,2-tetrafluoro-1-iodoethane in the presence of an inert solvent. In particular, the novel process can be used for the preparation of compounds of the formula III*. In the compounds of the formula III*, R* is halogen, formyl or a mesogenic group.

The reaction is carried out in the presence of an inert solvent, suitable solvents being the conventional solvents for reactions of phenoxides with alkyl halides, preferably polar aprotic solvents, in particular organic amides, such as, for example, dimethylamide (DMA), hexamethylphosphoric triamide (HMPTA) or N-methylpyrrolidone (NMP), or cyclic urea derivatives, such as, for example, N,N-dimethylpropyleneurea (DMPU) and in particular 1,3-dimethyl-2-imidazolidinone (DMEU).

It is also possible to add cosolvents, such as TMEDA or crown ethers, such as 18-crown-6, to these solvents. The amount of solvent is not crucial; in general, from 100 to 10,000 g of solvent per mole of phenoxide can be used.

The reaction in the novel process is simple to carry out, it being possible for the starting materials to be reacted, depending on the phenoxide used, at temperatures of from −20° to +200° C., preferably at from −20° to +150° C., and at superatmospheric pressure or reduced pressure, preferably at atmospheric pressure.

In an expedient procedure, the phenoxide is introduced into the reactor in an inert solvent and is warmed. 1,2,2,2-Tetrafluoro-1-iodoethane is added dropwise with stirring, generally over the course of from 0.2 to 24 hours, at from −20° C. to 100° C., and, if appropriate, the mixture is allowed to warm slowly to the boiling point of the solvent.

In general, from 0.8 to 1.5 mol, preferably from 0.9 to 1.2 mol, of 1,2,2,2-tetrafluoro-1-iodoethane are required per mole of the phenoxide to be reacted.

The reaction mixture is worked up and the products isolated in a conventional manner, for example by pouring the reaction mixture into water and/or ice or dilute acid and, after separating off the aqueous phase, isolating the 1,2,2,2-tetrafluoroethoxybenzene derivatives by distillation and/or crystallization.

Surprisingly, the novel process allows substituted 1,2,2,2-tetrafluoroethoxybenzene derivatives, which are valuable intermediates, for example for liquid crystals, auxiliaries, plant-protection agents pharmaceuticals, to be prepared in a simpler manner than in the prior art and in higher yields.

The compounds of the formula II can be prepared, for example, as shown in the synthesis schemes below:

Scheme 3

$(A = -(-A^1-Z^1)_m-A^2; Z^2 = -CH_2CH_2-)$

-continued
Scheme 3

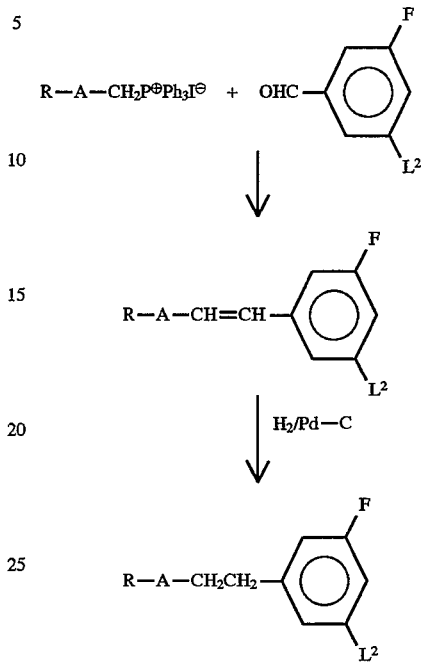

Scheme 4

$(A = -(-A^1-Z^1-)_m-A^2-; Z^2 = \text{single bond})$

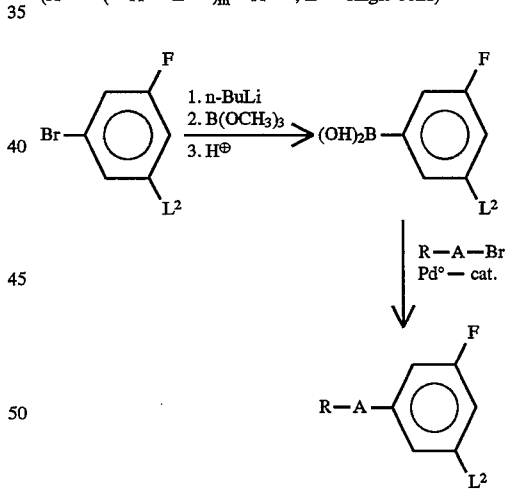

Scheme 5

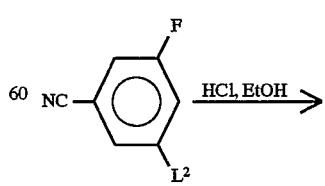

Scheme 5

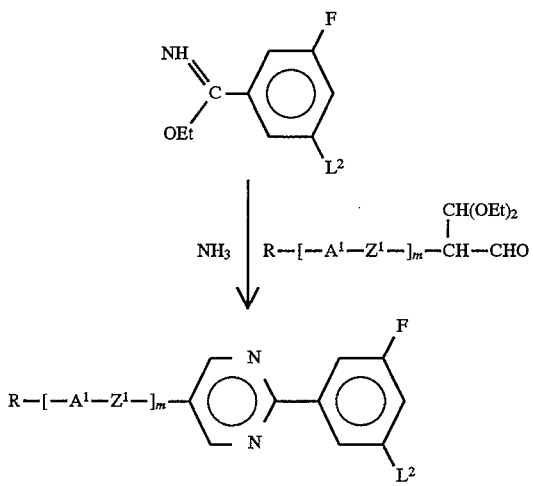

Scheme 6

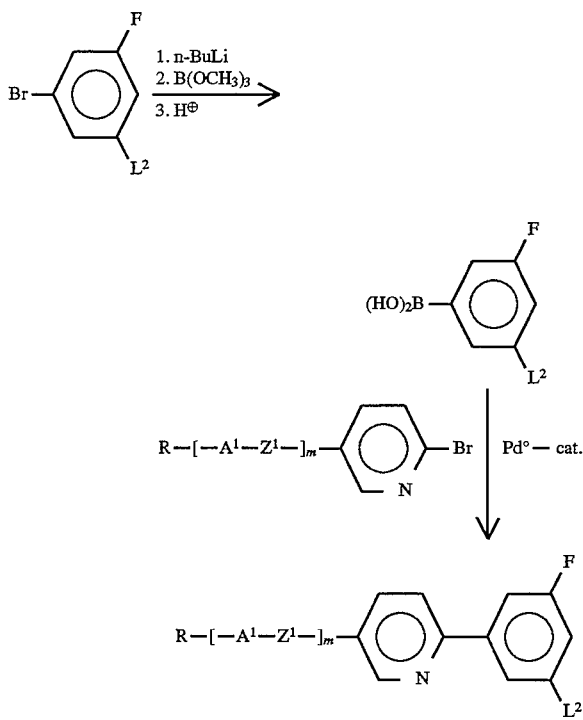

Scheme 7

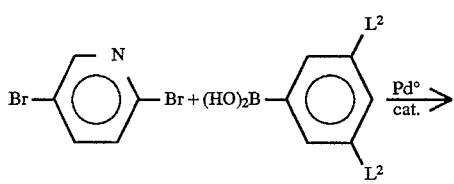

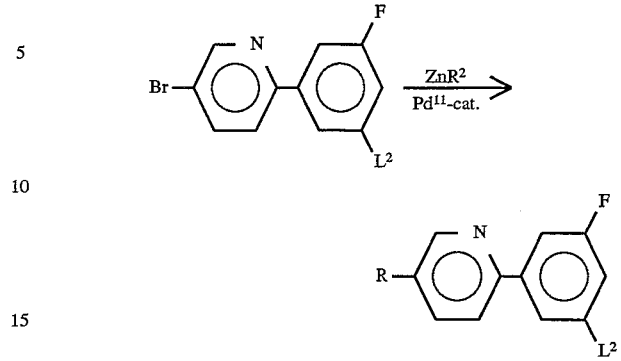

The starting materials are either known or can be prepared analogously to known compounds.

Esters of the formula I can also be obtained by esterification of corresponding carboxylic acids (or reactive derivatives thereof) using alcohols or phenols (or reactive derivatives thereof) or by the DCC method (DCC= dicyclohexylcarbodiimide).

The corresponding carboxylic acids and alcohols or phenols are known or can be prepared analogously to known processes.

In a further process for the preparation of the compounds of the formula I, an aryl halide is reacted with an olefin in the presence of a tertiary amine and in the presence of a palladium catalyst (cf. R. F. Heck, Acc. Chem. Res. 12(1979) 146). Examples of suitable aryl halides are chlorides, bromides and iodides, in particular bromides and iodides. The tertiary amines which are necessary for the success of the coupling reaction, such as, for example, triethylamine, are also suitable as solvent. Examples of suitable palladium catalysts are palladium salts, in particular Pd(II) acetate, with organophosphorus(III) compounds, such as, for example, triarylphosphines. The reaction can be carried out in the presence or absence of an inert solvent at temperatures between about 0° and 150°, preferably between 20° and 100°; suitable solvents are, for example, nitriles, such as acetonitrile, or hydrocarbons, such as benzene or toluene. The aryl halides and olefins employed as starting materials are frequently commercially available or can be prepared by processes known from the literature, for example by halogenation of corresponding parent compounds or by elimination reactions on corresponding alcohols or halides.

Stilbene derivatives, for example, can be prepared in this way. The stilbenes can also be prepared by reacting a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 (1986)).

Aromatic compounds can also be coupled by reacting aryl halides with aryltin compounds. These reactions are preferably carried out with addition of a catalyst, such as, for example, a palladium(O)complex, in inert solvents, such as hydrocarbons, at high temperatures, for example in boiling xylene under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I can also be prepared by Fritsch-Buttenberg-Wiechell rearrangement (Ann. 279, 319, 1984), in which 1,1-diaryl-2-haloethylenes are rearranged in the presence of strong bases to give diarylacetylenes.

Tolans of the formula I can also be prepared by brominating the corresponding stilbenes and then dehydrohalogenating the product. Use can also be made here of variants of this reaction which are not mentioned in greater detail.

Ethers of the formula I are obtainable by etherification of corresponding hydroxyl compounds, preferably corresponding phenols, the hydroxyl compound expediently first being converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This metal derivative can then be reacted with the appropriate alkyl halide, alkyl sulphonate or dialkyl sulphonate, expediently in an inert solvent, such as, for example, acetone, 1,2-dimethoxyethane, DMF or dimethyl sulphoxide or alternatively with an excess of aqueous or aqueous-alcoholic NaOH or KOH at temperatures between about 20° and 100° C.

The starting materials are either known or can be prepared analogously to known compounds.

The compounds of the formula I' in which $Z^2 =$—(CH$_2$)$_4$— can be prepared as shown in the following scheme:

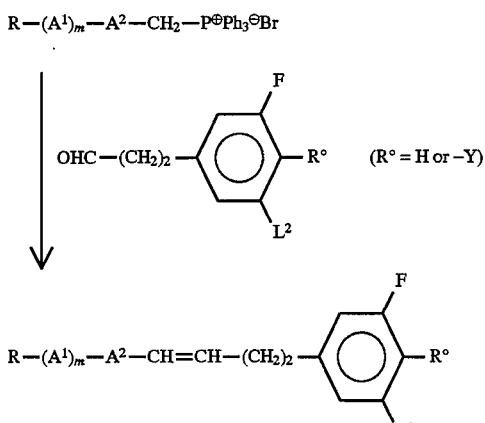

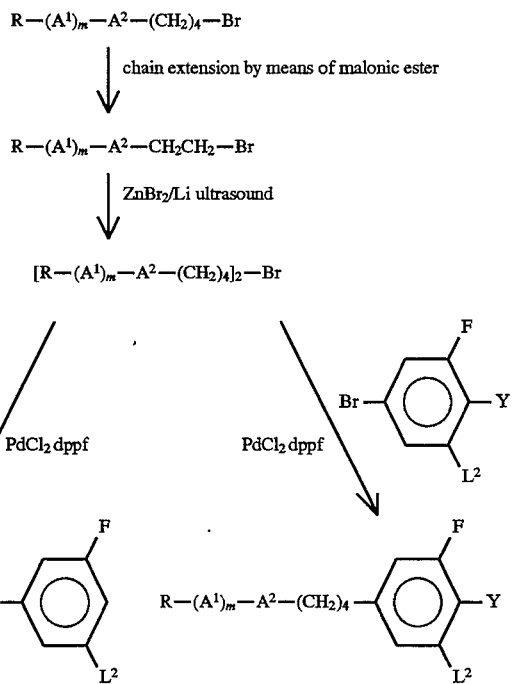

The Pd(II)-catalyzed coupling reaction either forms the target product I' directly or forms a precursor, into which the radical —Y is introduced completely analogously to the abovementioned methods for compounds of the formula I.

The compounds of the formula I' in which $Z^2=$—CH=CH—CH$_2$CH$_2$— can be prepared by the Wittig method as shown in the following scheme:

The preferred trans-isomers can be prepared by the isomerization methods known from the literature. Any intermediates obtained in which R°=H are converted into the compounds of the formula I' entirely analogously to the precursors of the compounds of the formula I by introduction of the radical —Y.

The aldehydes can be obtained by Heck reaction of appropriately substituted 1-bromo-3-fluorobenzene derivatives with allyl alcohol.

The synthesis of some particularly preferred compounds is shown in greater detail below:

Scheme 10
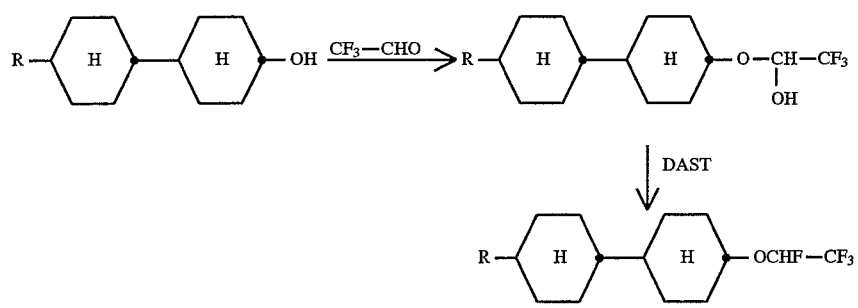
Scheme 11
(L² = H or F)
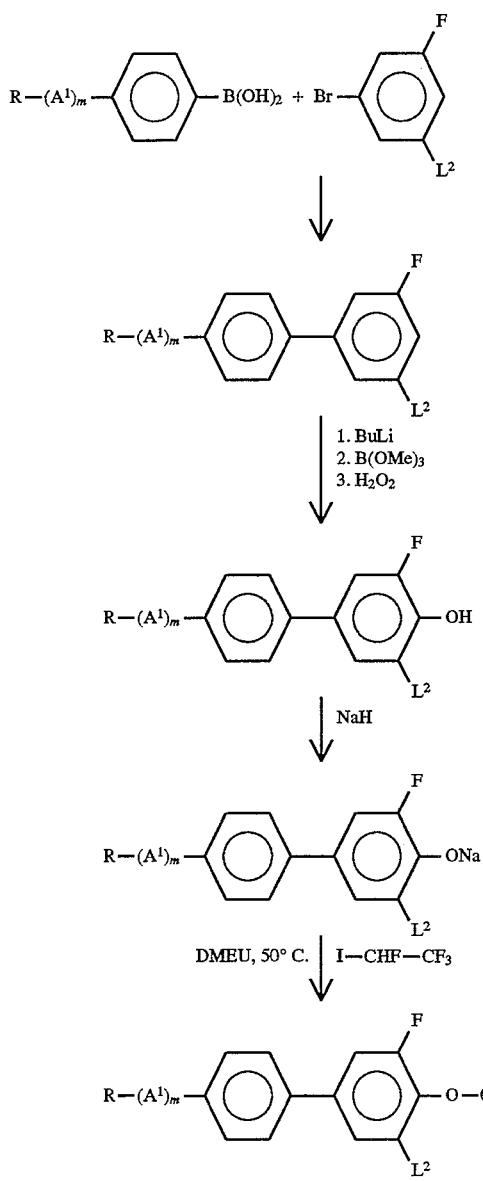
Scheme 12
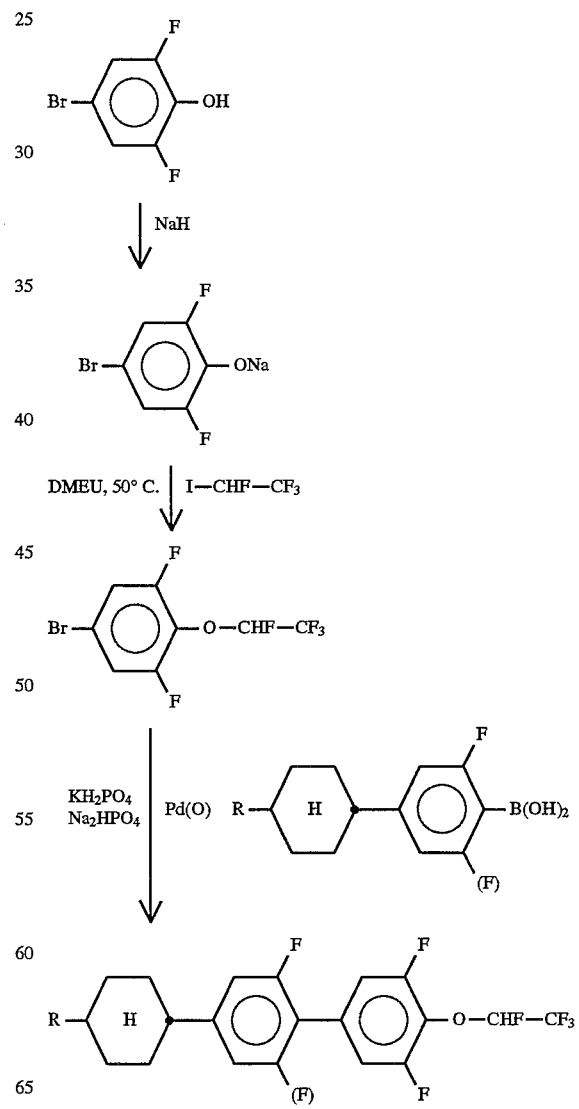

Scheme 13

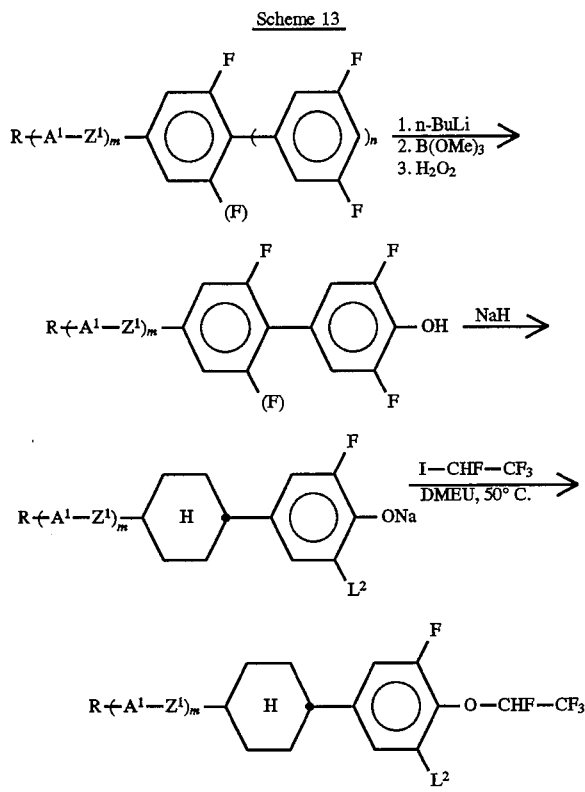

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances stances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexylesters of cyclohexylcyclohexanecarboxylic acid, cyclohexylphenyl esters of benzoic acid, of cyclohexanecarboxylic acid and of cyclohexylcyclo-hexanecarboxylic acid, phenylcyclohexanes, cyclohexylbiphenyls, phenylcyclohexylcyclohexanes, cyclohexylcyclohexanes, cyclohexylcyclohexenes, 1,4-bis-cyclohexylbenzenes, 4,4'-bis-cyclohexylbi-phenyls, phenyl- or cyclohexylpyrimidines, phenyl- or cyclo-hexylpyridines, phenyl- or cyclohexyldioxanes, phenyl- or cyclohexyl-1,3-dithianes, 1,2-diphenyl-ethanes, 1,2-dicyclohexylethanes, 1-phenyl-2-cyclo-hexylethanes, 1-cyclohexyl-2-(4-phenyl-cyclohexyl)-ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C_C—E—R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclo-hexylene or 1,4-cyclohexenylene, Pyr is pyrimidine-2,5-diyl or pyridine-2,5-diyl, Dio is 1,3-dioxane-2,5-diyl end G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cy-c-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_1$, where i 0 or 1, and k+1 is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this subgroup is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a-Sa and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5 to 90% and in particular 10 to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R- Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the alignment of the nematic phases.

In the present application and in the examples below, the structures of the liquid crystal compounds are indicated by acronyms, the transformation into chemical formulae being carried out as shown in Tables A and B below. All radicals $C_nH_{2n+1}$ are straight-chain alkyl radicals having n carbon atoms. The coding in Table B is self-evident. In Table A, only the acronym for the parent structure is shown. In each individual case, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_nH_{2n+1}$ | CF$_3$ | H | H |
| nCF$_3$ | $C_rH_{2r+1}$—CH=$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |
| nF.F.F | $C_nH_{2n+1}$ | F | F | F |

-continued

| Code for $R^1$, $R^2$, $L^1$, $L^2$ | $R^1$ | $R^2$ | $L^1$ | $L^2$ |
|---|---|---|---|---|
| nCl.F.F | $C_nH_{2n+1}$ | Cl | F | F |
| nCF$_3$.F.F | $C_nH_{2n+1}$ | CF$_3$ | F | F |
| nOCF$_3$.F.F | $C_nH_{2n+1}$ | OCF$_3$ | F | F |
| nOCF$_2$.F.F | $C_nH_{2n+1}$ | OCHF$_2$ | F | F |
| nOCF$_3$.F | $C_nH_{2n+1}$ | OCF$_3$ | F | H |

Table A:

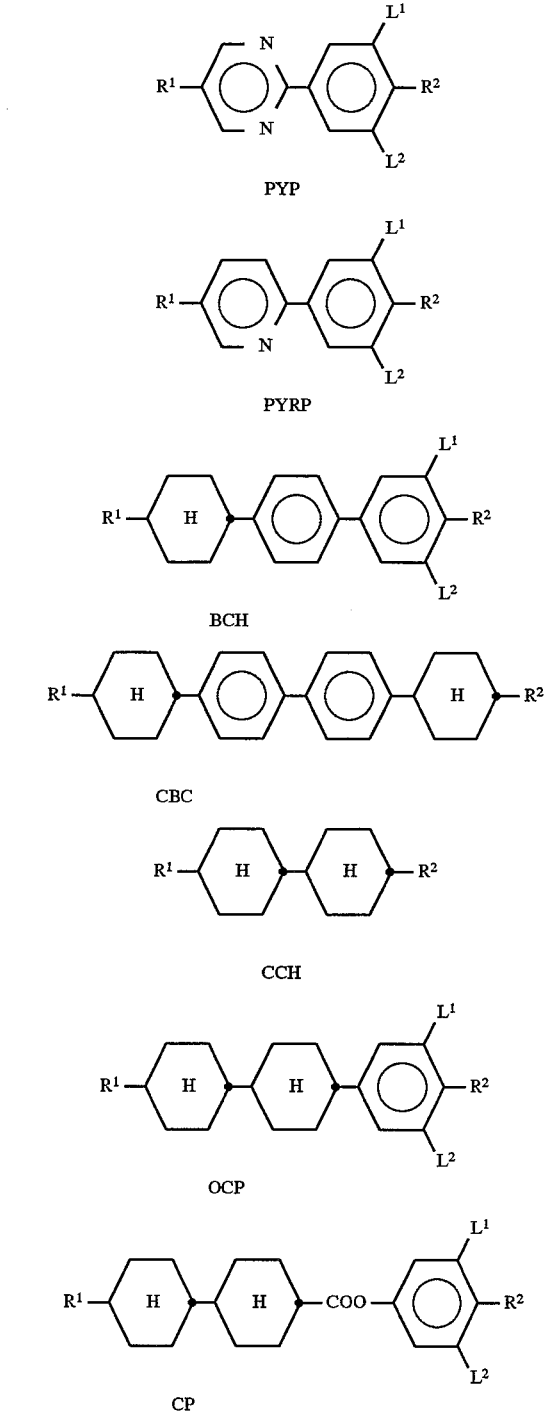

Table A:
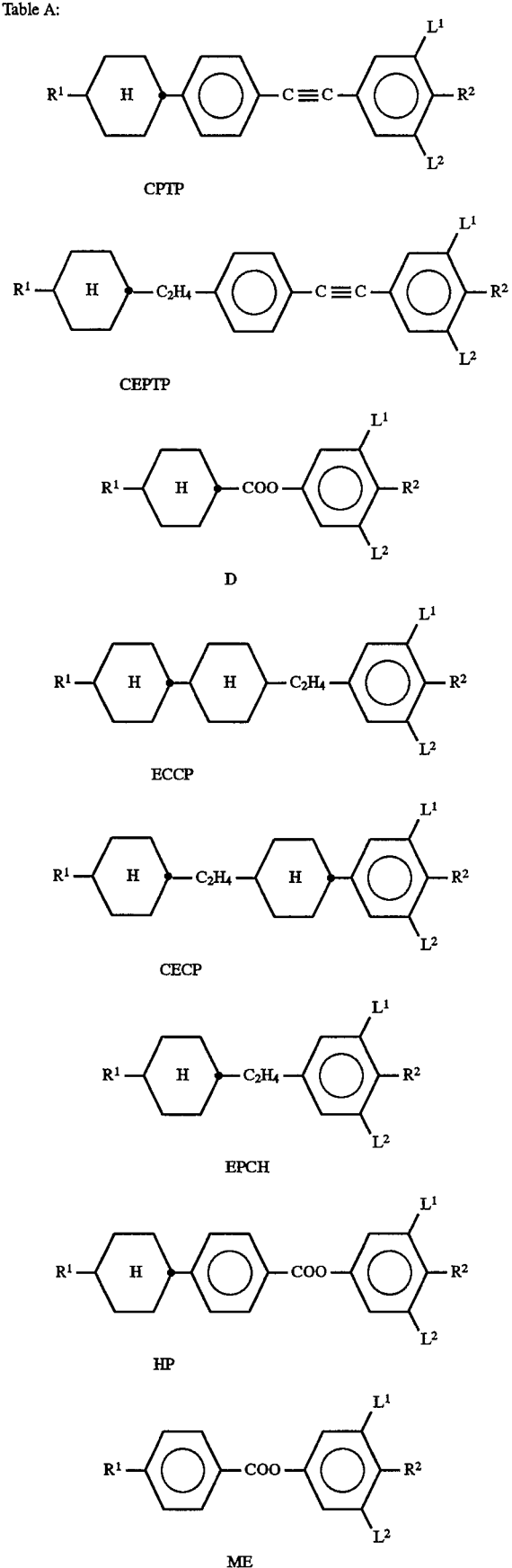
Table A:
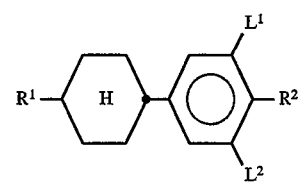

Table A:
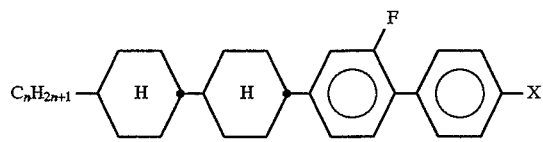
CCB-n.FX
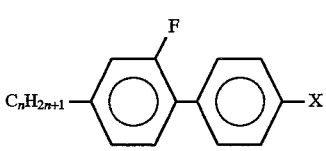
B-n.FX
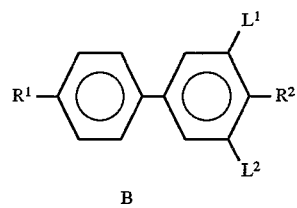
B
Table B:
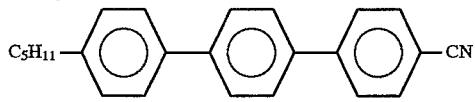
T15
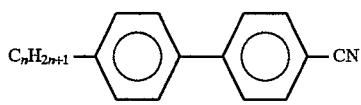
K3n
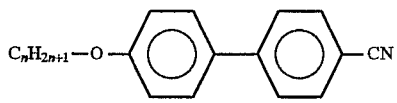
M3n
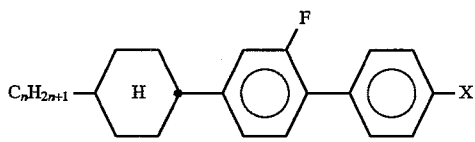
BCH-n.FX
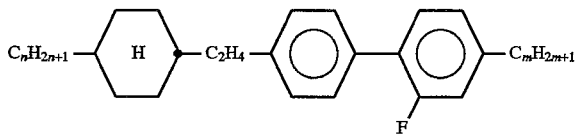
Inm
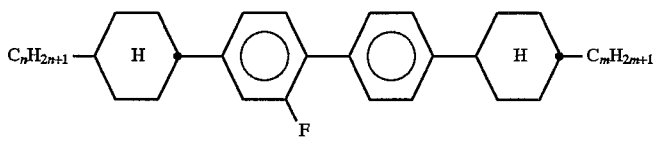
CBC-nmF Table B:
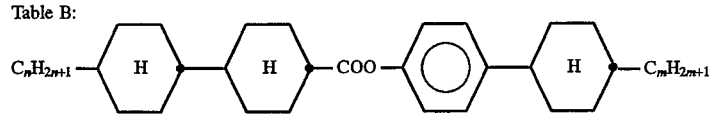
CCPC-nm
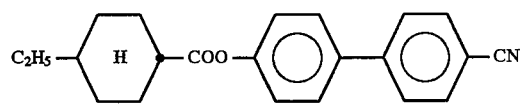
CHE
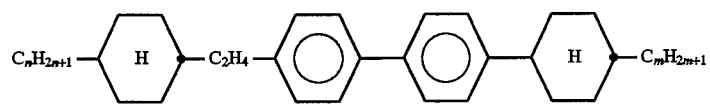
ECBC-nm
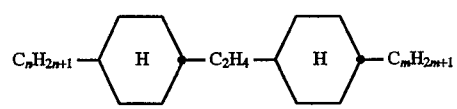
ECCH-nm
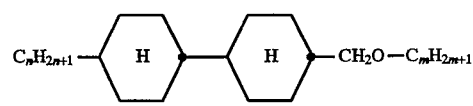
CCH-n1Em
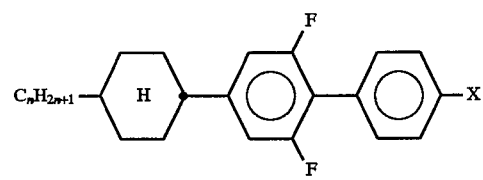
CUP-nX
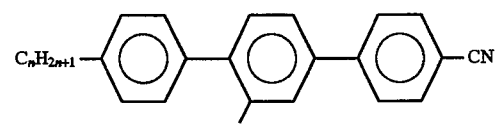
T-nFN
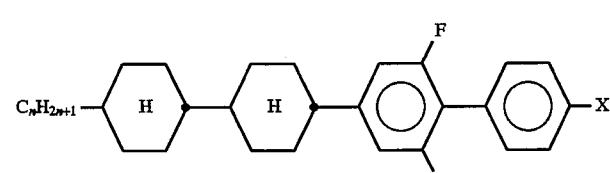
CCUP-nX
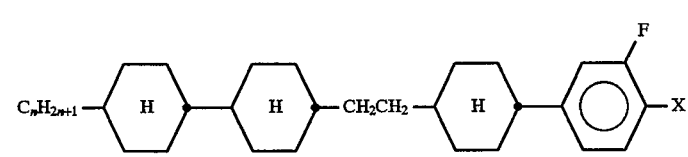
CCECP-nX.F Table B:

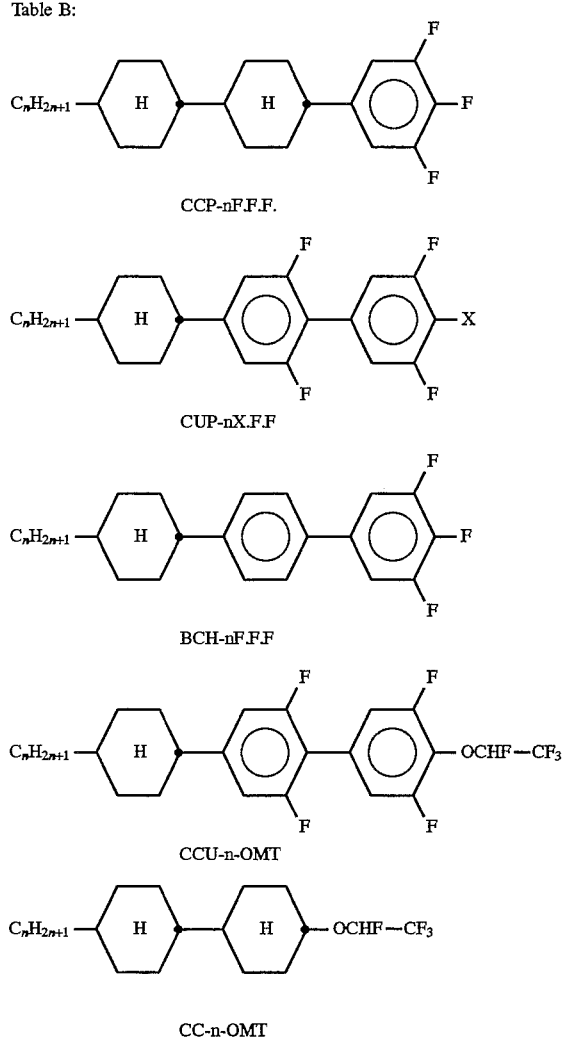

The examples below are intended to illustrate the invention without representing a limitation. Above and below, percentages are per cent by weight. All temperatures are given in degrees Celsius. m.p. denotes melting point, c.p.= clearing point. Furthermore, C=crystalline state, N=nematic phase, S=smectic phase and I=isotophic phase. The numbers between these symbols represent the transition temperatures. An denotes optical anisotropy (589 nm, 20° C.), and the viscosity ($mm^2$/ sec) was determined at 20° C.

"Customary work-up" means that water is added if appropriate, the mixture is extracted with dichloromethane, diethyl ether or toluene, the phases are separated, the organic phase is dried and evaporated, and the product is purified by distillation under reduced presssure or crystallization and/or chromatography. The following abbreviations are used:

DAST diethylaminosulphur trifluoride
DMEU 1,3-dimethyl-2-imidazolidinone
POT potassium tertiary-butanolate
THF tetrahydrofuran
pTSOH p-toluenesulphonic acid

EXAMPLE 1

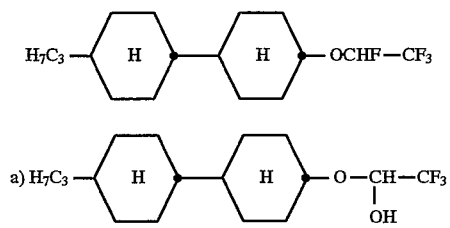

Trifluoroacetaldehyde (prepared from 20 ml of conc. $H_2SO_4$ and 0.17 mol of $CF_3$—$CH(OH)_2$) is passed at –50° C. into a solution comprising 0.1 mol of trans-4-(trans-4-n-propylcyclohexyl) cyclohexanol in 200 ml of dichloroethane. The mixture is stirred at –50° C. for 0.5 hour, and a spatula tip of potassium tert-butoxide is added to the mixture. The mixture is then stirred for a further 2 hours at –50° C. and allowed to warm to room temperature. The reaction mixture is evaporated and purified by flash chromatography.

b) 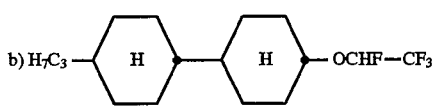

0.0756 mol of DAST is added dropwise at room temperature to 0.062 mol of the trifluorohydroxy ether from Example 1a) in 20 ml of dichloroethane. During the addition, the temperature of the reaction mixture should not exceed 30° C.

The mixture is stirred for 1 hour at room temperature and cooled to 0° C, and water is added in portions. The organic phase is separated off and subjected to conventional work-up. C 51 $S_B$ (45) I, $\Delta n=+0.034$; $\Delta\epsilon=7.08$ The following compounds of the formula

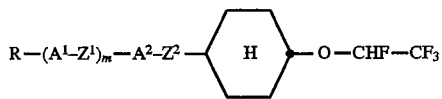

are obtained analogously:

| R | $-(A^1-Z^1)_m-A^2-Z^2-$ |
|---|---|
| CH$_3$ | 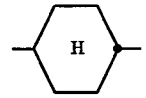 |
| C$_2$H$_5$ | 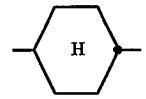 |
| n-C$_4$H$_9$ | 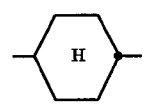 |
| n-C$_5$H$_{11}$ | 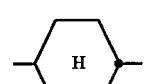 |
| n-C$_6$H$_{13}$ | 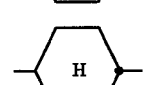 |
| n-C$_7$H$_{15}$ | 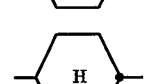 |
| CH$_3$ | 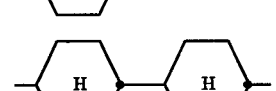 |
| C$_2$H$_5$ |  |
| n-C$_3$H$_7$ |  |
| n-C$_4$H$_9$ |  |
| n-C$_5$H$_{11}$ | |
| n-C$_6$H$_{13}$ | |
| n-C$_7$H$_{15}$ | |
| CH$_3$ | —OOC— |
| C$_2$H$_5$ | —OOC— |
| n-C$_3$H$_7$ | —OOC— |
| n-C$_5$H$_{11}$ | —OOC— |
| n-C$_6$H$_{13}$ | —OOC— |
| CH$_3$ | —COO— |
| C$_2$H$_5$ | —COO— |
| n-C$_3$H$_7$ | —COO— |
| n-C$_5$H$_{11}$ | —COO— |
| n-C$_6$H$_{13}$ | —COO— |
| CH$_3$ |  |

-continued

| R | $-(A^1-Z^1)_m-A^2-Z^2-$ |
|---|---|
| $C_2H_5$ | 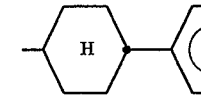 |
| n-$C_3H_7$ | 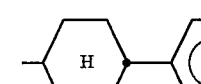 |
| n-$C_5H_{11}$ | 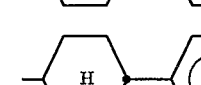 |
| n-$C_6H_{13}$ | 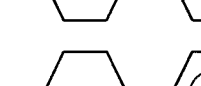 |
| $CH_3$ | 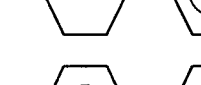 |
| $C_2H_5$ | 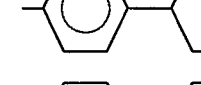 |
| n-$C_3H_7$ | 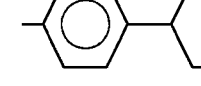 |
| n-$C_5H_{11}$ | 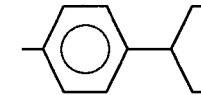 |
| n-$C_6H_{13}$ | 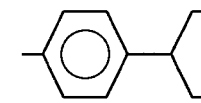 |
| $CH_3$ | 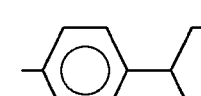 |
| $C_2H_5$ | 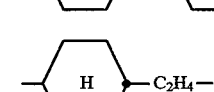 |
| n-$C_3H_7$ | 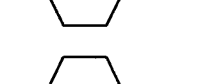 |
| n-$C_5H_{11}$ | 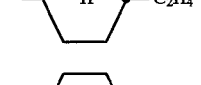 |
| n-$C_6H_{13}$ | 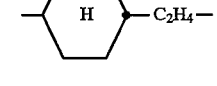 |

-continued

| R | $-(A^1-Z^1)_m-A^2-Z^2-$ |
|---|---|
| $CH_3$ | |
| $C_2H_5$ | |
| n-$C_3H_7$ | |
| n-$C_5H_{11}$ | |
| n-$C_6H_{13}$ | |

EXAMPLE 2

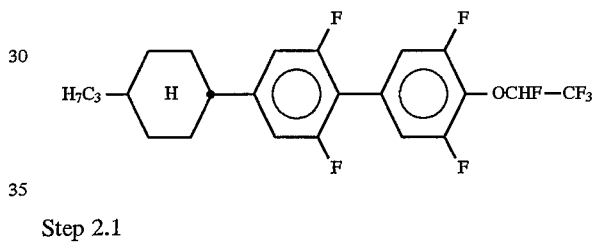

Step 2.1

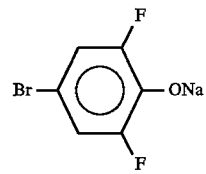

1.0 mol of sodium hydride (60%) is suspended in 200 ml of THF under nitrogen, and 1.0 mol of 4-bromo-2,6-difluorophenol, dissolved in 400 ml of THF, is added dropwise at 0° C. The mixture is allowed to warm to room temperature, and is stirred for 0.5 hour and filtered. The filtrate is evaporated, dissolved in toluene and concentrated until crystals form. The residue is precipitated using petroleum ether. The crystals are filtered off with suction and dried.

Step 2.2

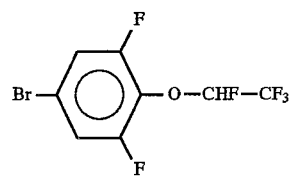

0.08 mol of the phenoxide from 2.1 are introduced into 80 ml of DMEU, and the mixture is heated to 50° C. 0.088 mol of 1,2,2,2-tetrafluoro-1-iodoethane is added, and the mixture is stirred at 50° C. for 16 hours and allowed to cool to room temperature, and water is added. The mixture is then acidified using dilute HCl and extracted with methyl tert-butyl ether and then with 10% NaOH and water, and the extract is dried over $Na_2SO_4$ and filtered. The filtrate is evaporated distilled at 800 mbar in a bulb tube. b.p. 145° C.

Step 2.3

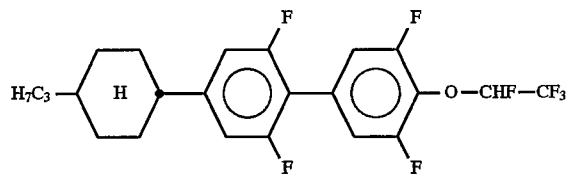

0.013 mol of 4-[1,2,2,2-tetrafluoroethoxy]-2,6-difluorodibromobenzene difluorodibromobenzene is dissolved in 50 ml of THF and heated to 60° C., and 0.012 mol of 4-(trans-4-propylcyclohexyl) -2,6-difluorophenylboronic acid and a solution comprising 0.013 mol of $KH_2PO_4$, 0.025 mol of $Na_2HPO_4$ and 25 ml of water are added. 0.012 mol of tetrakis[tri-phenylpalladium (0)] is added, and the mixture is stirred at 70° C. over night, allowed to cool to room temperature and subjected to conventional work-up. C 104 I; $\Delta n=+0.102$; $\Delta\epsilon=20.92$.

The following compounds of the formula

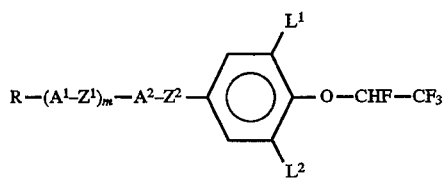

are prepared analogously:

| R | $-(A^1-Z^1)_m-A^2-Z^2-$ | $L^1$ | $L^2$ |
|---|---|---|---|
| $C_2H_5$ | 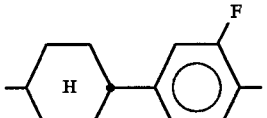 | H | H |
| $C_2H_5$ | 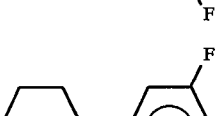 | F | H |
| $C_2H_5$ | 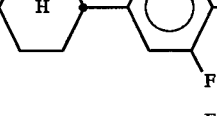 | F | F |
| n-$C_3H_7$ | 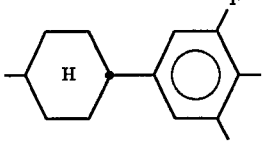 | H | H |
| n-$C_3H_7$ | 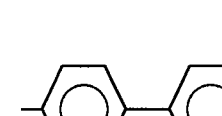 | F | H |
| n-$C_5H_{11}$ | 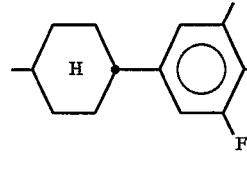 | H | H |
| n-$C_5H_{11}$ | 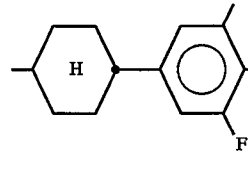 | F | H |
| n-$C_5H_{11}$ | 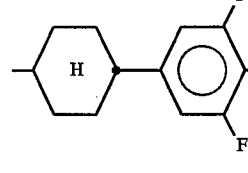 | F | F  C 98I; $\Delta\epsilon=$ 22.22; $\Delta n=$ +0.116 |
| n-$C_6H_{13}$ | 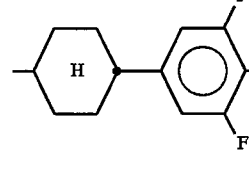 | H | H |
| n-$C_6H_{13}$ | 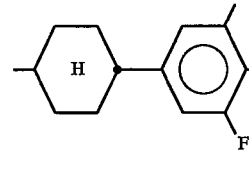 | F | H |
| n-$C_6H_{13}$ | 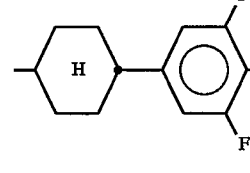 | F | F |
| $C_2H_5$ | 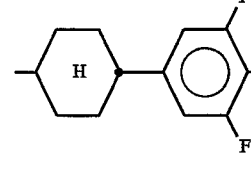 | H | H |

| R | $-(A^1-Z^1)_m-A^2-Z^2-$ | $L^1$ | $L^2$ |
|---|---|---|---|
| $C_2H_5$ | 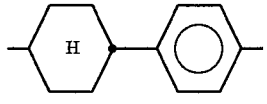 | F | H |
| $C_2H_5$ | 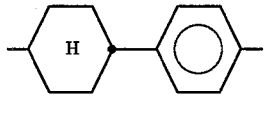 | F | F |
| n-$C_3H_7$ | 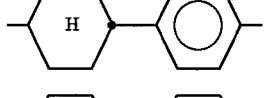 | H | H |
| n-$C_3H_7$ | 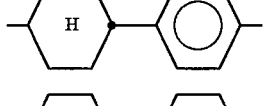 | F | H |
| n-$C_3H_7$ | 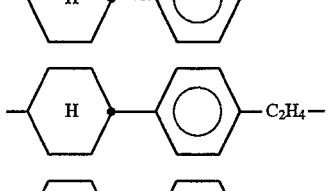 | F | F |
| n-$C_5H_{11}$ | 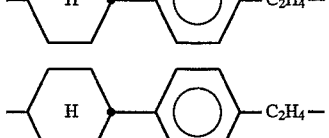 | H | H |
| n-$C_5H_{11}$ | 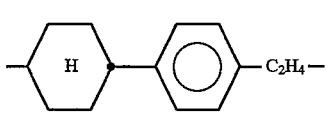 | F | H |
| n-$C_5H_{11}$ | 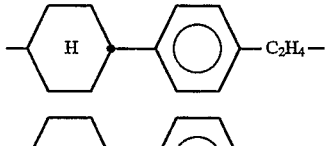 | F | F |
| $C_2H_5$ | 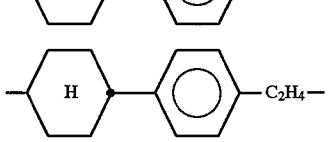 | H | H |
| $C_2H_5$ | 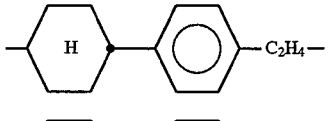 | H | F |
| $C_2H_5$ | 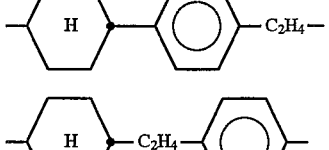 | F | F |
| n-$C_3H_7$ |  | H | H |
| n-$C_3H_7$ | | H | F |
| n-$C_3H_7$ | | F | F |
| n-$C_5H_{11}$ | | H | H |
| n-$C_5H_{11}$ | | H | F |
| n-$C_5H_{11}$ | | F | F |
| $C_2H_5$ | | H | H |
| $C_2H_5$ | | H | F |
| $C_2H_5$ | | F | F |
| n-$C_3H_7$ | | H | H |
| n-$C_3H_7$ | | H | F |
| n-$C_3H_7$ | | F | F |
| n-$C_5H_{11}$ | | H | H |
| n-$C_5H_{11}$ | | H | F |
| n-$C_5H_{11}$ | | F | F |
| $C_2H_5$ |  | H | H |

| R | $-(A^1-Z^1)_m-A^2-Z^2-$ | $L^1$ | $L^2$ |
|---|---|---|---|
| $C_2H_5$ | 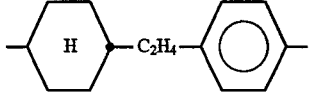 | H | F |
| $C_2H_5$ | 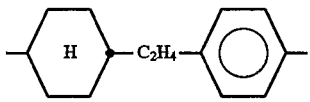 | F | F |
| n-$C_3H_7$ | 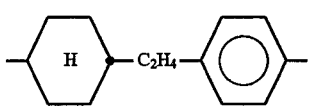 | H | H |
| n-$C_3H_7$ | 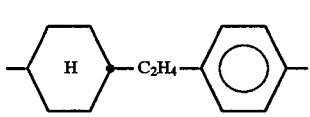 | H | F |
| n-$C_3H_7$ |  | F | F |
| n-$C_5H_{11}$ | 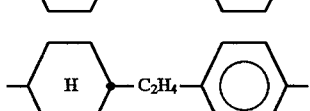 | H | H |
| n-$C_5H_{11}$ |  | H | F |
| n-$C_5H_{11}$ |  | F | F |
| $C_2H_5$ | 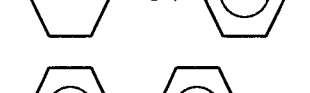 | H | H |
| $C_2H_5$ |  | H | F |
| $C_2H_5$ | 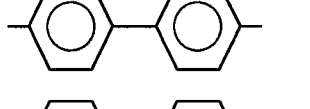 | F | F |
| n-$C_3H_7$ | 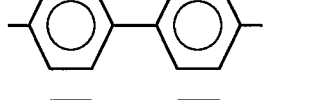 | H | H |
| n-$C_3H_7$ | 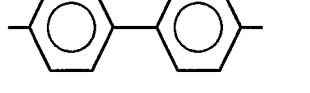 | H | F |
| n-$C_3H_7$ | 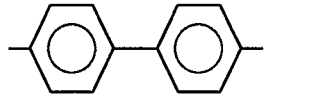 | F | F |
| R | $-(A^1-Z^1)_m-A^2-Z^2-$ | $L^1$ | $L^2$ |
|---|---|---|---|
| n-$C_5H_{11}$ | 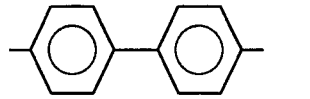 | H | H |
| n-$C_5H_{11}$ | 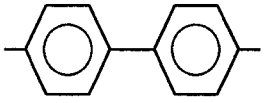 | H | F |
| n-$C_5H_{11}$ | 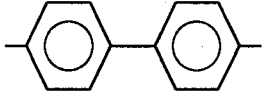 | F | F |
| $C_2H_5$ | 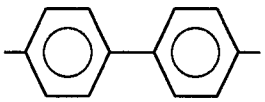 | H | H |
| $C_2H_5$ | 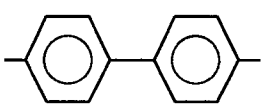 | H | F |
| $C_2H_5$ | 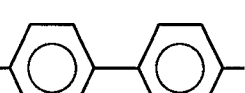 | F | F |
| n-$C_3H_7$ | 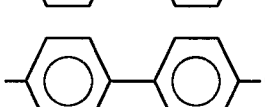 | H | H |
| n-$C_3H_7$ |  | H | F |
| n-$C_3H_7$ |  | F | F |
| n-$C_5H_{11}$ |  | H | H |
| n-$C_5H_{11}$ |  | H | F |
| n-$C_5H_{11}$ | 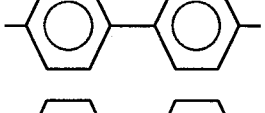 | F | F |
| n-$C_3H_7$ | 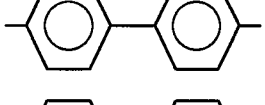 | H | H |
| n-$C_3H_7$ | 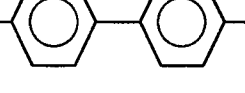 | H | F |

5,643,495
43
-continued
| R | $-(A^1-Z^1)_m-A^2-Z^2-$ | $L^1$ | $L^2$ |
|---|---|---|---|
| n-C₃H₇ | 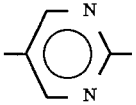 | F | F |
| n-C₅H₁₁ | 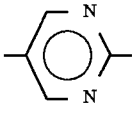 | H | H |
| n-C₅H₁₁ | 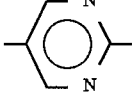 | H | F |
| n-C₅H₁₁ | 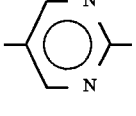 | F | F |
| n-C₃H₇ | 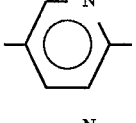 | H | H |
| n-C₃H₇ | 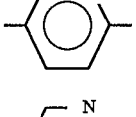 | H | F |
| n-C₃H₇ | 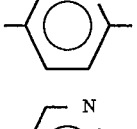 | F | F |
| n-C₅H₁₁ | 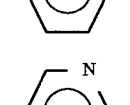 | H | H |
| n-C₅H₁₁ | 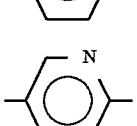 | H | F |
| n-C₅H₁₁ | 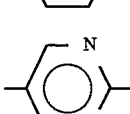 | F | F |
| C₂H₅ |  | H | H |
| C₂H₅ | 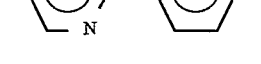 | H | F |
| C₂H₅ | 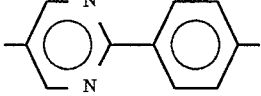 | F | F |
44
-continued
| R | $-(A^1-Z^1)_m-A^2-Z^2-$ | $L^1$ | $L^2$ |
|---|---|---|---|
| n-C₃H₇ | 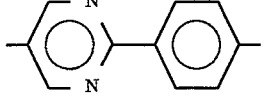 | H | H |
| n-C₃H₇ | 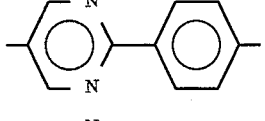 | H | F |
| n-C₃H₇ | 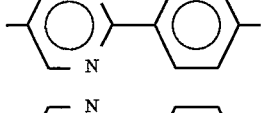 | F | F |
| n-C₅H₁₁ | 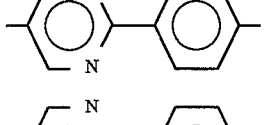 | H | H |
| n-C₅H₁₁ | 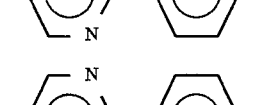 | H | F |
| n-C₅H₁₁ | 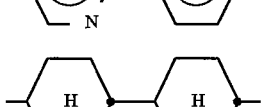 | F | F |
| —C₂H₅ |  | H | H |
| —C₂H₅ | 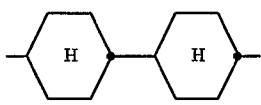 | H | F |
| —C₂H₅ | 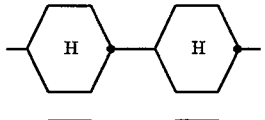 | F | F |
| n-C₃H₇ | 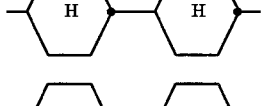 | H | H |
| n-C₃H₇ |  | H | F |
| n-C₃H₇ |  | F | F |
| n-C₄H₉ |  | H | H |
| n-C₄H₉ | | H | F |

-continued

| R | −(A¹−Z¹)ₘ−A²−Z²− | L¹ | L² |
|---|---|---|---|
| n-C₄H₉ | H—H | F | F |
| n-C₅H₁₁ | H—H | H | H |
| n-C₅H₁₁ | H—H | H | F |
| n-C₅H₁₁ | H—H | F | F |
| C₂H₅ | ⌬ (phenyl) | H | H |
| C₂H₅ | ⌬ | H | F |
| C₂H₅ | ⌬ | F | F |
| n-C₃H₇ | ⌬ | H | H |
| n-C₃H₇ | ⌬ | H | F |
| n-C₃H₇ | ⌬ | F | F |
| n-C₅H₁₁ | ⌬ | H | H |
| n-C₅H₁₁ | ⌬ | H | F |
| n-C₅H₁₁ | ⌬ | F | F |
| C₂H₅ | H | H | H |
| C₂H₅ | H | H | F |

-continued

| R | −(A¹−Z¹)ₘ−A²−Z²− | L¹ | L² |
|---|---|---|---|
| C₂H₅ | H | F | F |
| n-C₃H₇ | H | H | H |
| n-C₃H₇ | H | H | F |
| n-C₃H₇ | H | F | F |
| n-C₅H₁₁ | H | H | H |
| n-C₅H₁₁ | H | H | F |
| n-C₅H₁₁ | H | F | F |
| n-C₃H₇ | H—H—C₂H₄— | H | H |
| n-C₃H₇ | H—H—C₂H₄— | H | F |
| n-C₃H₇ | H—H—C₂H₄— | F | F |
| n-C₅H₁₁ | H—H—C₂H₄— | H | H |
| n-C₅H₁₁ | H—H—C₂H₄— | H | F |
| n-C₅H₁₁ | H—H—C₂H₄— | F | F |
| C₂H₅ | dioxane—H | H | H |

-continued

| R | $-(A^1-Z^1)_m-A^2-Z^2-$ | $L^1$ | $L^2$ |
|---|---|---|---|
| $C_2H_5$ | 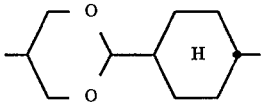 | H | F |
| $C_2H_5$ | 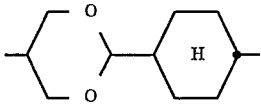 | F | F |
| $n$-$C_3H_7$ | 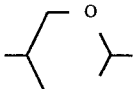 | H | H |
| $n$-$C_3H_7$ | 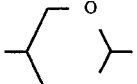 | H | F |
| $n$-$C_3H_7$ | 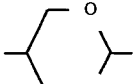 | F | F |
| $n$-$C_5H_{11}$ | 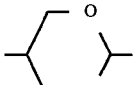 | H | H |
| $n$-$C_5H_{11}$ | 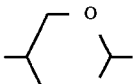 | H | F |
| $n$-$C_5H_{11}$ | 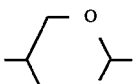 | F | F |

MIXTURE EXAMPLES

EXAMPLE A

| | | |
|---|---|---|
| PCH-5F | 9.50% | Clearing point [°C.]: 90.6 |
| PCH-6F | 7.60% | $\Delta n$ [589 nm, 20° C.]: 0.0975 |
| PCH-7F | 5.70% | $\Delta \epsilon$ [1 kHz, 20° C.]: 6.11 |
| CCP-2OCF$_3$ | 7.60% | |
| CCP-3OCF$_3$ | 11.40% | |
| CCP-4OCF$_3$ | 8.55% | |
| CCP-5OCF$_3$ | 8.55% | |
| BCH-3F.F | 8.55% | |
| BCH-5F.F | 11.40% | |
| ECCP-3OCF$_3$ | 9.50% | |
| ECCP-5OCF$_3$ | 4.75% | |
| CBC-33F | 1.90% | |
| CBC-53F | 1.90% | |
| CBC-55F | 1.90% | |
| CUU-5-OMT | 5.00% | |

EXAMPLE B

| | | |
|---|---|---|
| PCH-5F | 9.50% | Clearing point [°C.]: 89% |
| PCH-6F | 7.60% | $\Delta n$ [589 nm, 20° C.]: 0.0968 |
| PCH-7F | 5.70% | $\Delta \epsilon$ [1 kHz, 20° C.]: 6.05 |
| CCP-2OCF$_3$ | 7.60% | |
| CCP-3OCF$_3$ | 11.40% | |
| CCP-4OCF$_3$ | 8.55% | |
| CCP-5OCF$_3$ | 8.55% | |
| BCH-3F.F | 8.55% | |
| BCH-5F.F | 11.40% | |
| ECCP-3OCF$_3$ | 9.50% | |
| ECCP-5OCF$_3$ | 4.75% | |
| CBC-33F | 1.90% | |
| CBC-53F | 1.90% | |
| CBC-55F | 1.90% | |
| CUU-3-OMT | 5.00% | |

EXAMPLE C

| | | |
|---|---|---|
| PCH-5F | 9.0% | Clearing point [°C.]: 83.9 |
| PCH-6F | 7.2% | $\Delta n$ [589 nm, 20° C.]: 0.0906 |
| PCH-7F | 5.4% | $\Delta \epsilon$ [1 kHz, 20° C.]: 5.42 |
| CCP-2OCF$_3$ | 7.2% | |
| CCP-3OCF$_3$ | 10.8% | |
| CCP-4OCF$_3$ | 8.1% | |
| CCP-5OCF$_3$ | 8.1% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| CC-3-OMT | 10.0% | |

We claim:
1. A 1,2,2,2-Tetrafluoroethyl ether of formula I

$$R-(A^1-Z^1)_m-A^2-Z^2-A^3-O-CHF-CF_3 \qquad I$$

in which

R is H, an alkyl or alkenyl radical having 1 to 15 carbon atoms which is unsubstituted, monosubstituted by CN or $CF_3$ or at least monosubstituted by halogen, and one or more $CH_2$ groups in these radicals is optionally replaced, in each case independently of one another, by —O—, —S—,

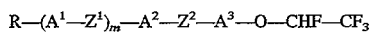

—CO—, —CO—O—, —O—CO— or —O—CO—O— in such a way that O atoms are not linked directly to one another, $A^1$, $A^2$ and $A^3$ are each, independently of one another,
(a) a trans-1,4-cyclohexylene radical in which, in addition, one or more non-adjacent $CH_2$ groups is optionally replaced by —O— and/or —S—,
(b) a 1,4-phenylene radical in which, in addition, one or two CH groups is optionally replaced by N,
(c) a radical from the group consisting of 1,4-cyclohexenylene, 1,4-bicyclo[2.2.2.]octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) are optionally substituted by one or two fluorine atoms, $Z^1$ and $Z^2$ are each, independently of one another, —CO—O—, —O—CO—, —CH$_2$O—, —OCH$_2$—CH$_2$CH$_2$—, —CH=CH—, —C≡C— or a single bond, one of the radicals $Z^1$ and $Z^2$ also being —(CH$_2$)$_4$— or —CH=CH—CH$_2$CH$_2$—, and m is 0,1 or 2.

2. A compound according to claim 1, of formula I'

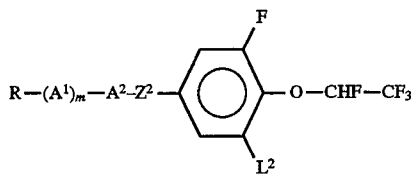

in which $L^2$ is H or F.

3. A compound according to claim 1, of formula I1

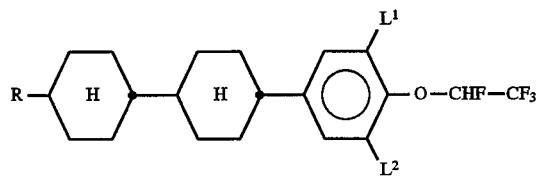

in which $L^1$ and $L^2$ are each, independently of one another, H or F.

4. A compound according to claim 1, of formula I3

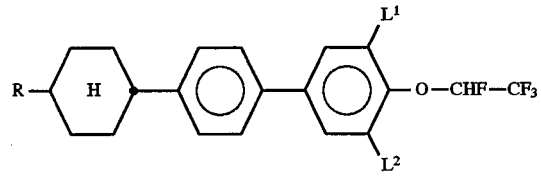

in which $L^1$ and $L^2$ are each, independently of one another, H or F.

5. A compound according to claim 1, of formula I12

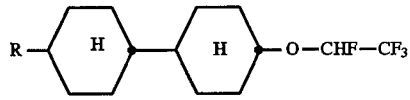

6. A compound according to claim 1, of the formula

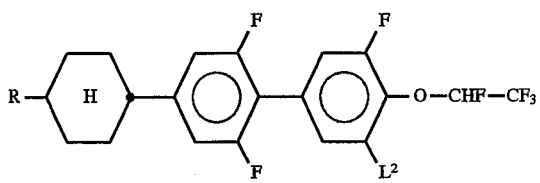

in which $L^2$ is H or F.

7. A compound according to claim 1, of the formula

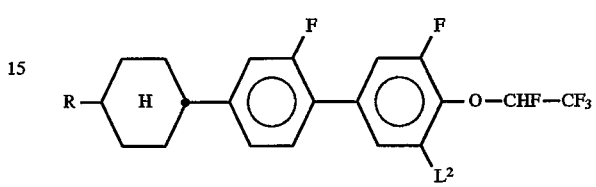

in which $L^2$ is H or F.

8. A process for the preparation of substituted 1,2,2,2-tetraluoroethoxybenzene from the corresponding phenoxide, comprising reacting the phenoxide with 1,2,2,2-tetrafluoro-1-iodoethane in the presence of an inert solvent.

9. A process according to claim 8 for the preparation of a 1,2,2,2-tetrafluoroethylphenyl ether of formula III*

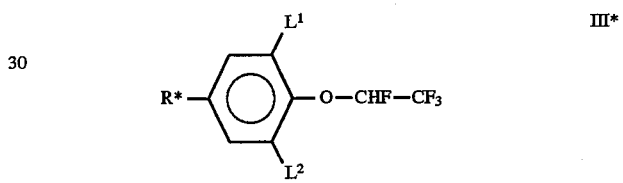

in which R* is halogen, formyl or a mesogenic group, and $L^1$ and $L^2$ are each, independently of one another, H or F, said process comprising reacting a corresponding phenoxide with 1,2,2,2-tetrafluoro-1-iodoethane in the presence of an inert solvent.

10. A process according to claim 9, wherein the inert solvent used is a polar aprotic solvent.

11. A process according to claims 9, wherein the solvent used is an organic amide or a cyclic urea derivative.

12. A process according to claim 11, wherein the solvent used is 1,3-dimethyl-2-imidazolidinone (DMEU).

13. A liquid-crystal medium comprising at least two liquid-crystalline components, wherein at least one component is at least one compound of formula I of claim 1.

14. A liquid-crystal display element, containing a liquid-crystalline medium according to claim 13.

15. In a method for producing an electro-optical display using a dielectric, the improvement wherein the dielectric contains a liquid-crystalline medium according to claim 13.

* * * * *